(12) United States Patent
Barker (10) Patent No.: US 7,899,553 B2
(45) Date of Patent: Mar. 1, 2011

(54) LEAD ANCHOR FOR IMPLANTABLE STIMULATION DEVICES

(75) Inventor: John Michael Barker, Ventura, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 389 days.

(21) Appl. No.: 11/692,772

(22) Filed: Mar. 28, 2007

(65) Prior Publication Data

US 2008/0243220 A1    Oct. 2, 2008

(51) Int. Cl.
*A61N 1/04* (2006.01)
(52) U.S. Cl. ......... 607/126; 600/375; 600/386; 607/130; 607/149
(58) Field of Classification Search ................. 607/116, 607/122, 126, 128–130, 145, 149, 150; 600/372–375, 377, 381; 604/174, 175, 178; 606/139, 205–208, 219–220, 157, 158; 128/DIG. 26; 24/455, 484
See application file for complete search history.

(56) References Cited

U.S. PATENT DOCUMENTS

| | | | | |
|---|---|---|---|---|
| 4,066,085 A | * | 1/1978 | Hess | 607/131 |
| 4,177,818 A | * | 12/1979 | De Pedro | 607/130 |
| 4,553,961 A | | 11/1985 | Pohndorf et al. | |
| 4,672,979 A | | 6/1987 | Pohndorf | |
| 4,683,895 A | * | 8/1987 | Pohndorf | 606/232 |
| 4,913,164 A | * | 4/1990 | Greene et al. | 607/126 |
| 5,107,856 A | | 4/1992 | Kristiansen et al. | |
| 5,242,431 A | | 9/1993 | Kristiansen | |
| 5,525,805 A | | 6/1996 | Greenly | |
| 5,746,722 A | | 5/1998 | Pohndorf et al. | |
| 5,843,146 A | | 12/1998 | Cross, Jr. | |
| 5,931,861 A | | 8/1999 | Werner et al. | |
| 5,957,968 A | | 9/1999 | Belden et al. | |
| 6,134,447 A | | 10/2000 | Havinis et al. | |
| 6,178,356 B1 | * | 1/2001 | Chastain et al. | 607/128 |
| 6,181,969 B1 | | 1/2001 | Gord | |
| 6,308,104 B1 | | 10/2001 | Taylor et al. | |
| 6,473,654 B1 | | 10/2002 | Chinn | |
| 6,516,227 B1 | | 2/2003 | Meadows et al. | |
| 6,609,029 B1 | | 8/2003 | Mann et al. | |
| 6,609,032 B1 | | 8/2003 | Woods et al. | |
| 6,610,074 B2 | * | 8/2003 | Santilli | 606/158 |
| 6,741,892 B1 | | 5/2004 | Meadows et al. | |
| 6,901,287 B2 | | 5/2005 | Davis et al. | |
| 6,951,550 B2 | * | 10/2005 | Bierman | 604/174 |
| 7,244,150 B1 | | 7/2007 | Brase et al. | |
| 2003/0212435 A1 | * | 11/2003 | Gold et al. | 606/206 |

(Continued)

OTHER PUBLICATIONS

Compact Oxford English Dictionary (Definition: "pin").*

(Continued)

*Primary Examiner* — Mark W Bockelman
*Assistant Examiner* — Erica Lee
(74) *Attorney, Agent, or Firm* — Frommer Lawrence & Haug LLP; Patrick R. Turner (57) ABSTRACT

Disclosed is a lead anchor comprising a body made of an elastomeric material and defining a first opening and a second opening through which a lead can pass, one or more fasteners disposed within the body, with the ends of the fasteners protruding from the body, wherein the ends are configured and arranged to be clamped down to secure a lead passing through the body.

20 Claims, 5 Drawing Sheets

U.S. PATENT DOCUMENTS

| | | |
|---|---|---|
| 2004/0059392 A1 | 3/2004 | Parramon et al. |
| 2004/0199122 A1* | 10/2004 | Bierman et al. .............. 604/174 |
| 2004/0254623 A1* | 12/2004 | Rodriguez et al. ............ 607/115 |
| 2005/0004590 A1* | 1/2005 | Waters et al. ................. 606/170 |
| 2006/0161237 A1* | 7/2006 | Cawthra ........................ 607/129 |
| 2007/0150007 A1 | 6/2007 | Anderson et al. |
| 2007/0150036 A1 | 6/2007 | Anderson |
| 2007/0219595 A1 | 9/2007 | He |
| 2007/0239243 A1 | 10/2007 | Moffitt et al. |

OTHER PUBLICATIONS

U.S. Appl. No. 11/238,240, filed Sep. 29, 2005.

* cited by examiner

LEAD ANCHOR FOR IMPLANTABLE STIMULATION DEVICES

FIELD

The invention is directed to one piece lead anchors for implantable stimulation devices, as well as the implantable stimulation devices, and methods of manufacture and use of the lead anchors and the implantable stimulation devices.

BACKGROUND

Tissue (e.g., neural or muscular tissue) stimulation is a well accepted clinical method for reducing pain in certain populations of patients. Implantable stimulation devices have been developed to provide therapy for a variety of treatments. For example, implantable stimulation devices can be used to stimulate nerves, such as the spinal cord, muscles, or other tissue. An implantable stimulation device typically includes an implantable control module with a pulse generator (although in some instances the control module or pulse generator may not be implanted), a lead, and an array of stimulator electrodes. The stimulator electrodes are implanted in contact with or near the nerves, muscles, or other tissue to be stimulated. The pulse generator in the control module generates electrical pulses that are delivered by the electrodes to body tissue. As an example, electrical pulses can be provided to the dorsal column fibers, or other neural tissue, within the spinal cord to provide spinal cord stimulation.

The stimulator electrodes are coupled to the control module by the lead and the control module is implanted elsewhere in the body, for example, in a subcutaneous pocket. The lead is often anchored at one or more places in the body to prevent or reduce movement of the lead or stimulator electrodes within the body which could damage tissue, move the stimulator electrodes out of the desired position, or interrupt the connection between the stimulator electrodes and the control module.

Ideally, lead anchors should be constructed of strong, biocompatible materials and should be small, light-weight and easy to use. Many conventional lead anchors are difficult to use without being overly invasive. Most use sutures to secure the lead anchor to the surrounding tissue in order to keep it in place. One problem suturing an anchor in place is that the sutures should be tight enough to keep the lead anchor from being dislodged, but not so tight as to damage the lead itself, which could result in lead failure. This requires a level of skill on the part of the clinician, which necessitates practice before the clinician is able to consistently install the lead anchor properly. In addition, it often requires substantial surgical time to properly secure the lead anchor.

Conventional lead anchors may not sufficiently grip the lead to keep the lead in place. As a consequence, the lead may migrate away from the intended stimulation site.

BRIEF SUMMARY

One embodiment is a lead anchor comprising a body made of an elastomeric material and defining a first opening and a second opening through which a lead can pass, one or more fasteners disposed within the body, with the ends of the fasteners protruding from the body, wherein the ends are configured and arranged to be clamped down to secure a lead passing through the body.

Another embodiment is a method of implanting an implantable stimulation device, the method comprising implanting a lead comprising an electrode array at the distal end of the lead extending from the electrode array, and anchoring the lead to the surrounding tissue using at least one lead anchor, wherein the lead anchor comprises a body made of an elastomeric material defining a first opening and a second opening through which the lead passes and one or more fasteners disposed within the body, with ends of the fasteners protruding from the body to anchor the lead to surrounding tissue.

Another embodiment is a surgical crimping tool that may be used to attach a lead anchor to a patient's tissue. The surgical crimping tool includes at least two gripping elements for squeezing together the protruding ends of a lead anchor; and a retention hook coupled to the gripping elements. The retention hook is configured and arranged to position the lead anchor relative to the gripping elements to clear a lead disposed in the lead anchor.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

FIG. 4 A is a schematic perspective view of a surgical crimping tool suitable for use according to the invention; the tool is depicted before implantation, when the fastener legs are open;

FIG. 4 B is a schematic perspective view of a surgical crimping tool suitable for use according to the invention; the tool is depicted after implantation, when the fastener legs are closed;

FIG. 4C is a blow-up view of the retention hook of the surgical crimping tool of FIGS. 4A and B.

DETAILED DESCRIPTION

The present invention is directed to the area of lead anchors used with implantable devices such as spinal cord stimulators, as well as methods of using lead anchors and implantable devices. In addition, the invention is directed to a surgical crimping tool used to secure a lead anchor to a patients' tissue.

A lead anchor can be used in an implantable device, such as an implantable spinal cord stimulator, to anchor a lead connecting a control module to an electrode array. The lead passes through the lead anchor, which is designed to prevent or reduce the likelihood that the lead will move within the lead anchor. Preferably, the lead anchor applies gentle compression to the lead to hold the lead in place.

One embodiment is a lead anchor including a body defining a first opening and a second opening through which a lead can pass. One or more fasteners are attached to the body. The fasteners are used to attach the lead anchor to tissue at the intended stimulation site and may also provide a controlled compressive load against the lead, thereby gripping the lead to keep the lead in place and prevent migration of the lead away from the intended stimulation site. The two legs of the fasteners are initially spread apart on either side of the anchor. In a preferred embodiment, the legs have sharpened ends so they are capable of piercing tissue. For insertion, the lead is threaded through one opening of the anchor and out through the other opening. After the lead is in place, the anchor is attached to a patient's tissue by squeezing the exposed fastener ends into the tissue. In addition to locking the anchor in place, squeezing the exposed ends of the fastener together may also generate compression on the lead, gripping the lead to protect against lead migration.

The anchor body may be made of any elastomeric material suitable for implantation into a patient's body. The material is preferably compressible so as to compress against the lead when the fasteners are in the closed position. In some embodiments, the body is made of silicone, polyurethane, or a combination thereof.

The fasteners can be any suitable component that can be configured and arranged to facilitate attachment of the lead anchor to surrounding tissue by squeezing ends of the fastener. In a preferred embodiment, the fastener is a staple. The fasteners may be made of any material that is suitable for implantation into a patient's body. In a preferred embodiment, the fasteners are made of any metal suitable for implantation into a patient's body. In one embodiment, the fasteners are inserted through the anchor body such that the two legs of the fastener are spread apart on either side of the anchor prior to implantation. In at least some embodiments, a portion of the fasteners is molded into the body when the body is formed.

The exposed fastener ends may be squeezed (i.e., closed) to attach the lead anchor to a patient's tissue with any suitable surgical tool. In one embodiment, the fasteners are closed with a hemostat. In another embodiment, the fasteners are closed with a surgical clamp. In another embodiment, the fasteners are closed by squeezing the exposed ends of the fasteners together with a special surgical crimping tool provided with the lead anchor. The surgical crimping tool may comprise a pair of handles fastened at a hinge element to form squeeze grips, and a retention hook, where the surgical crimping tool can squeeze together the exposed ends of the one or more surgical fasteners of a lead anchor, and the retention hook allows the surgical crimping tool to clear the lead and thus avoid damage to the lead. The special surgical crimping tool may incorporate a travel stop to prevent over-crimping of the fasteners, which could damage the lead and/or the tissue to which the lead anchor is attached. In at least some embodiments, the surgical crimping tool also contains a retention hook upon which the lead anchor sits while attaching the fasteners to the tissue. The retention hook facilitates proper spacing between the crimping tool and the lead anchor, so as to close the fasteners without damage to the lead or possible injury to the patient. In at least some embodiments, the lead anchor provides a constant lateral compression force between the fasteners, anchor body and lead.

In some embodiments, the hole in the anchor body through which the lead is threaded provides a slight interference fit relative to the lead during the threading process. In other embodiments, the hole in the anchor body through which the lead is threaded is a clearance fit relative to the lead during the threading process.

In another embodiment of the present invention, kits that contain one or more lead anchors and optionally a surgical crimping tool for attaching the lead anchor to a patient's tissue are provided. Optionally, the kit contains the entire implantable stimulation system or portions thereof, including one or more of a control module, an electrode array, a lead for coupling the control module to the electrode array, one or more lead anchors, and a surgical crimping tool for attaching the lead anchor to a patient's tissue.

Figure 1:
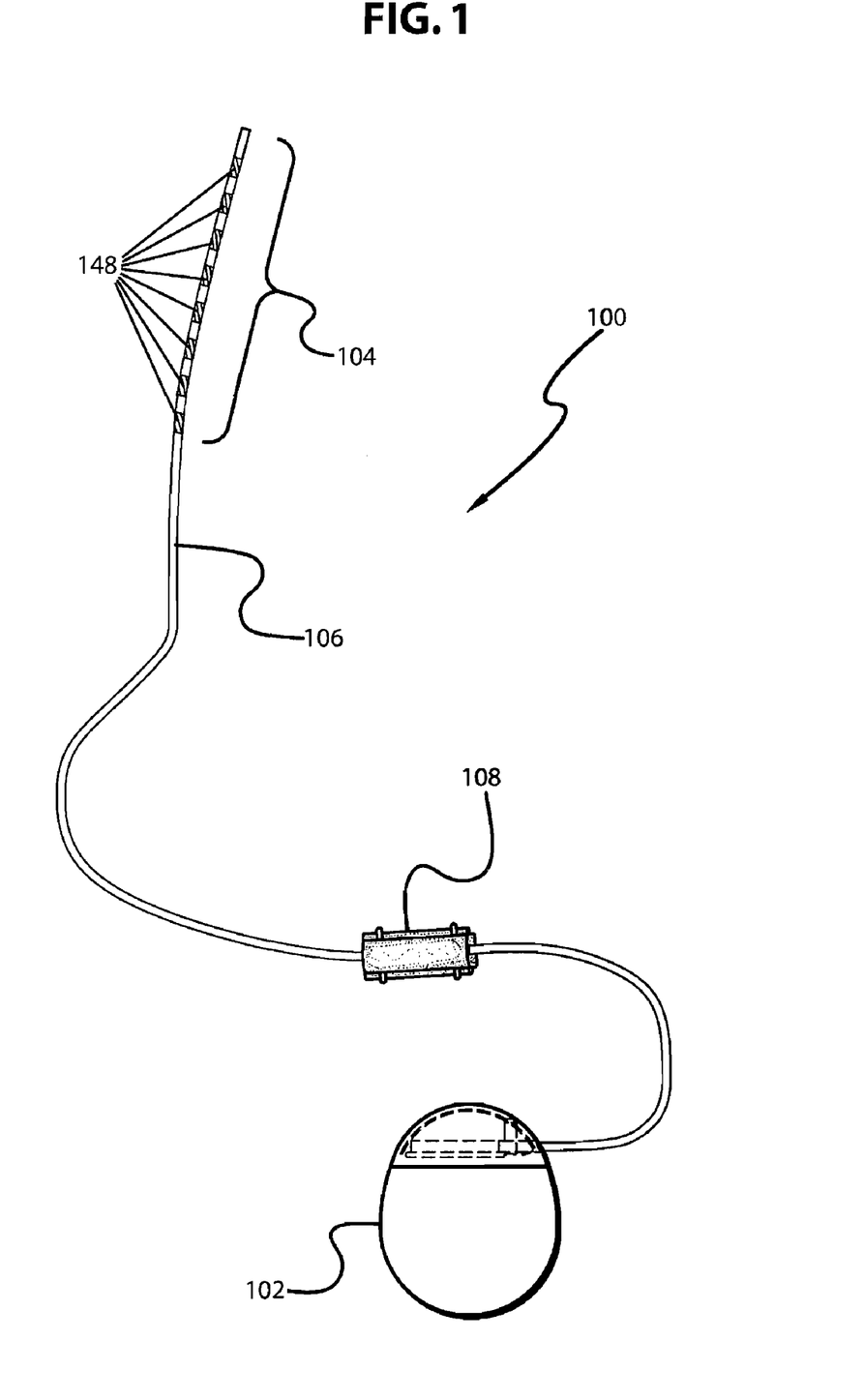
FIG. 1 is a schematic plan view of an implantable stimulator arrangement, including a lead anchor according to the invention.

FIG. 1 illustrates schematically an implantable stimulation device 100, such as a spinal cord stimulator. The implantable stimulation device includes a control module 102, an electrode array 104 of stimulator electrodes, a lead 106 coupling the control module to the electrode array, and one or more lead anchors 108. The control module 102 typically includes a pulse generator that provides pulses of stimulation current to electrodes of the electrode array 104. The control module 102 may also include a power source for generating the stimulation current or may receive power from an external source. The power source can be any available power source including batteries, such as primary batteries or rechargeable batteries. Examples of other power sources include, but are not limited to, super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

The control module 102 is optionally programmable to allowing programming of one or more functions such as, for example, the selection of electrodes for stimulation, the selection of electrodes as anode or cathode, the amplitude of the stimulation current, the duration of the stimulation current, and the periodicity of the stimulation current. In some embodiments, the control module 102 can be accessed using a programming unit external to the body of the patient to alter or modify these functions.

The electrode array 104 typically includes two or more electrodes. In some embodiments, the electrode array includes four, six, eight, 10, 16, or more electrodes. The electrodes can be in a linear array, for example, disposed along an electrode lead, or in a two-dimensional array, for example, forming two or more columns or rows, or any other arrangement. Non-limiting examples of suitable electrode arrays are illustrated in U.S. Pat. No. 6,516,227, incorporated herein by reference.

Electrodes leads with electrode arrays include, for example, percutaneous leads, cuff leads, and paddle leads. Examples of stimulation systems with electrode leads are described in, for example, U.S. Pat. Nos. 6,181,969; 6,516,227; 6,609,029; 6,609,032; and 6,741,892; and U.S. patent application Ser. Nos. 11/238,240; 11/319,291; 11/327,880; 11/375,638; 11/393,991; and 11/396,309, all of which are incorporated herein by reference. The lead 106 typically includes a set of conductors (for example, one conductor per electrode of the electrode array) within a non-conductive sheathing. The sheathing may be made of a flexible, biocompatible material.

Figure 2:
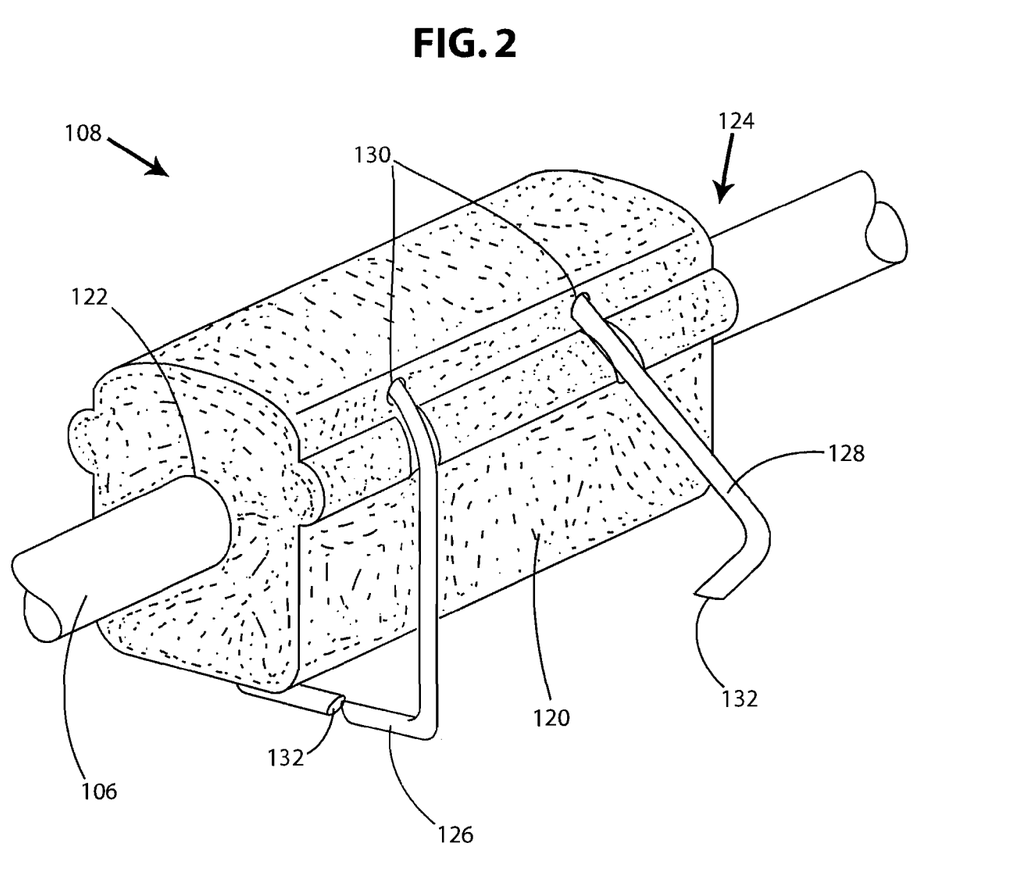
FIG. 2 is a schematic exterior perspective view of one embodiment of a lead anchor, according to the invention.
Figure 3A:
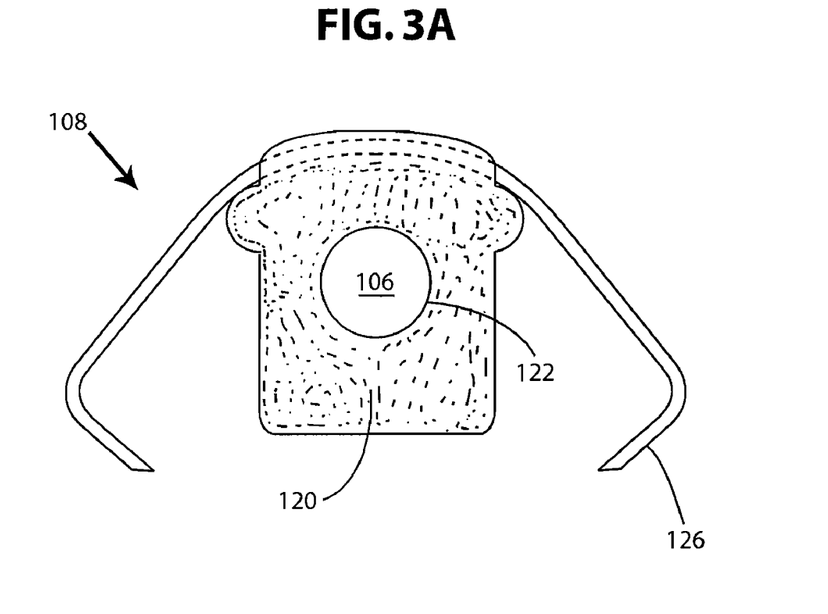
FIG. 3A is a schematic cross-sectional view of the lead anchor of FIG. 2 showing a fastener in the "open" position, prior to implantation.
Figure 3B:
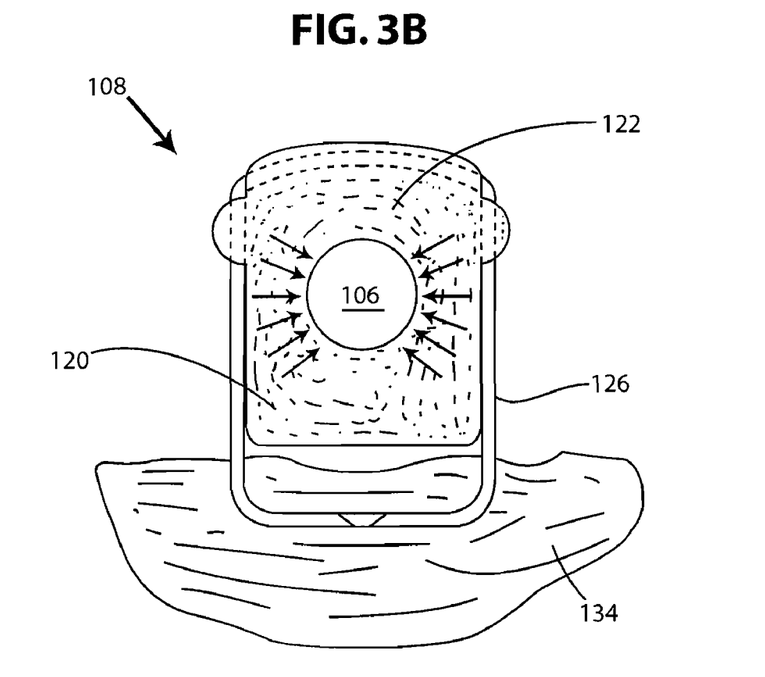
FIG. 3B is a schematic cross-sectional view of the lead anchor of FIG. 2 showing a fastener in the "closed" position, after implantation.

One or more lead anchors according to the present invention can be used to attach the lead to surrounding tissues to prevent or resist movement of the lead within the body of the patient when the lead anchor is attached to surrounding tissue. FIGS. 2-3B illustrate one embodiment of a lead anchor 108. The lead anchor includes a body 120 that is open at two ends 122, 124 to allow the lead 106 to pass through the lead anchor. The body has one or more fasteners 126 and 128 attached to it. In the embodiment illustrated in FIG. 2, the body 120 has two fasteners 126. The fasteners 126 are each inserted into the body 120 through holes 130 preferably in the top of the body, on the side opposite from where the lead anchor 108 is to be attached to a patient's tissue. It will be understood that the fastener can be placed in other parts of the lead body as well. The fasteners can be inserted so that the exposed legs of the fasteners run along two sides of the lead anchor 108. In at least some embodiments, the fastener ends with a pair of sharpened points 132 to facilitate piercing a patient's tissue. In the embodiment illustrated in FIG. 2, the front fastener 126 is in the closed position with the exposed legs squeezed together, and the rear fastener 128 is in the open position with legs spread apart.

The embodiment illustrated in FIG. 3A shows the lead anchor 108 showing a fastener 126 in the "open" position, prior to implantation. The embodiment illustrated in FIG. 3B shows the lead anchor 108 with a fastener 126 in the "closed" position, after attachment to a patient's tissue 134. Arrows depict compression of the lead 106 by the anchor body 120.

The anchor body 120 can be formed using a plastic or elastomeric material. Preferably, this material is biocompatible, durable, and suitable for implantation in a patient over an expected period of time. Also, the material is preferably elastomeric and compressible. Examples of suitable materials include silicone and polyurethane.

The anchor body 120 can be formed using an available technique including, for example, molding techniques. Portions of the fastener may be molded into the body as illustrated in FIGS. 2, 3A, and 3B.

The length of the lead anchor 108 can be selected for the particular purpose. In some embodiments, for example, for spinal cord stimulation, the lead anchor may have a length in the range of 4 to 10 millimeters. This length may be shorter or longer than other available lead anchors, depending on the specific application.

Figures 4A, 4B, 4C:
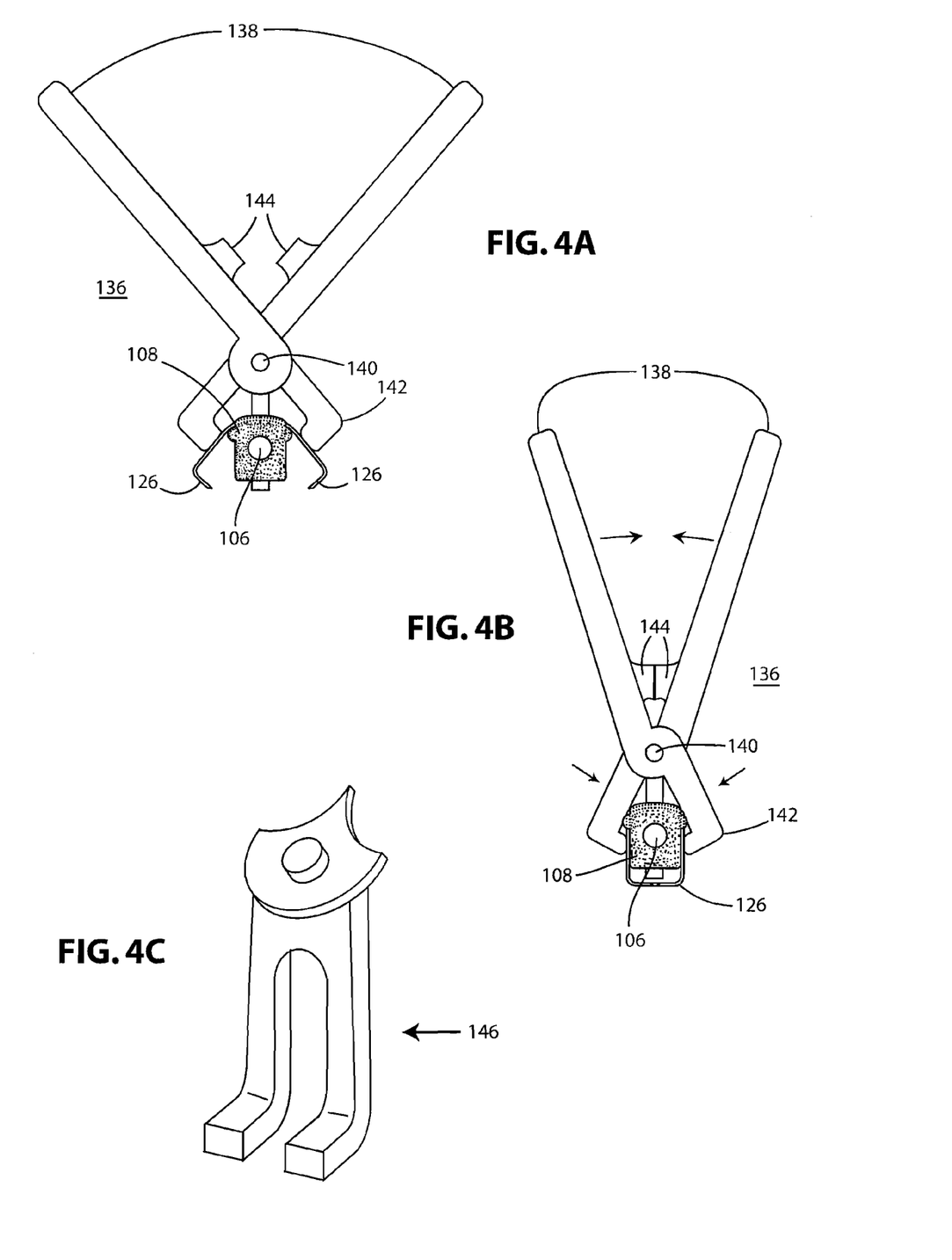
Figure 5:
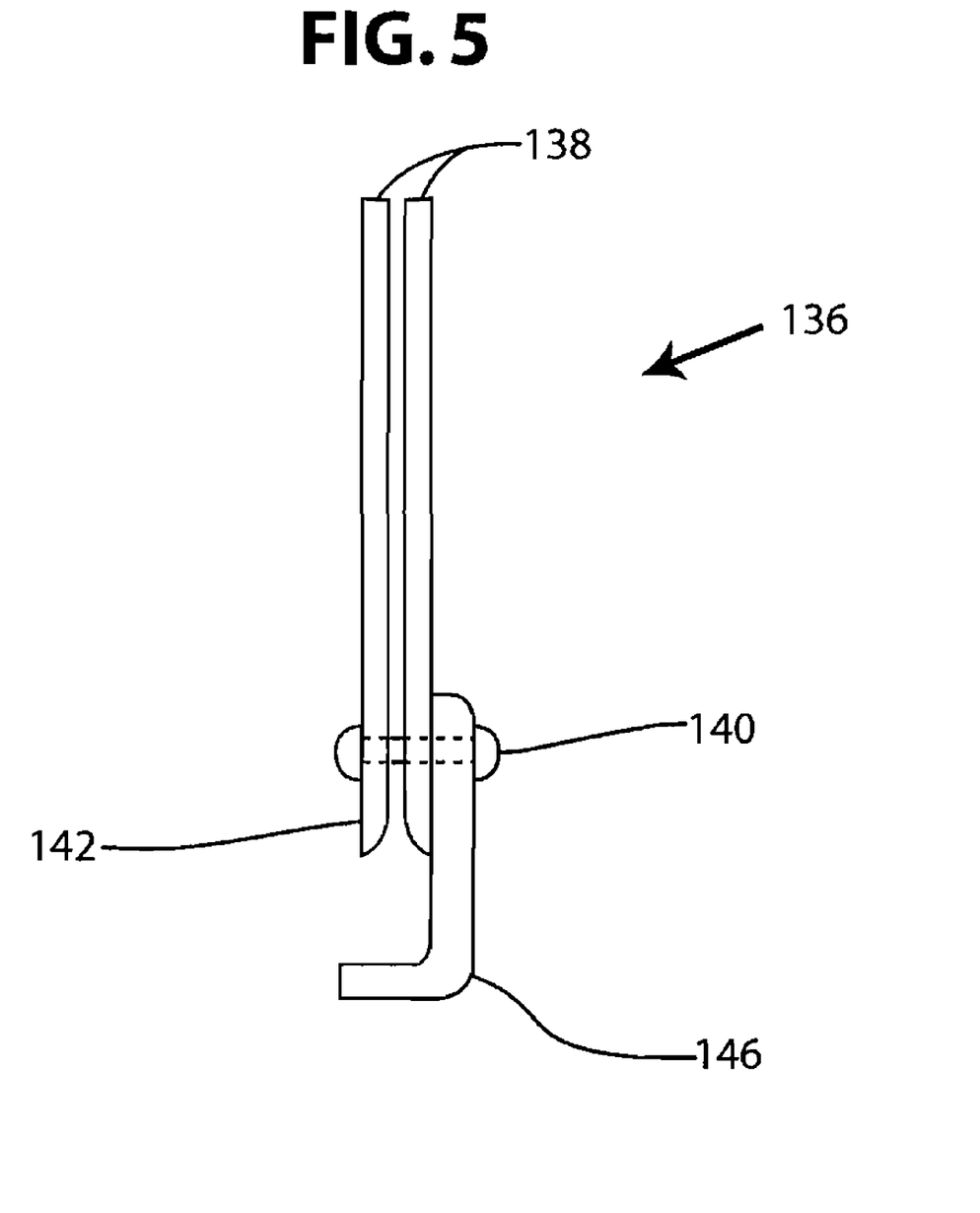
FIG. 5 is a side view of the surgical crimping tool of FIGS. 4A and B.

Lead anchors according to the invention may be secured to a subject patient's tissue by squeezing the exposed fastener ends towards each other and into the tissue by using a tool, e.g. a surgical clamp or hemostat. In a preferred embodiment, the lead anchor is secured by using a surgical crimping tool 136 according to the invention. FIGS. 4A-C and 5 illustrate one embodiment of a surgical crimping tool 136. The surgical crimping tool 136 includes a pair of handles 138 fastened at a hinge element 140 to form squeeze grips 142. The surgical crimping tool preferably contains a travel stop 144, to stop the crimping action of the surgical crimping tool 136 when the fastener 126 has been closed sufficiently to secure the lead anchor 108 to the patient's tissue and at the same time prevent damage to the lead 106 or the patient's tissue that may result from over-crimping. In at least some embodiments, the surgical crimping tool 136 also contains a retention hook 146 upon which the lead anchor can be placed. This positions the squeeze grips 142 relative to the fastener(s) 126, so as to close the fasteners 126 without damaging the lead 106 and possible injury to the patient. In one embodiment, the retention hook 146 is attached or otherwise coupled to the pair of handles 138 (for example, coupled at the hinge element 140 as illustrated in FIGS. 4C and 5) and extends below the squeeze grips 142 to provide a platform upon which the lead anchor 108 can be placed while closing the fasteners, as illustrated in FIGS. 4B and 5. In the embodiment illustrated in FIG. 4C, the retention hook 146 includes two parallel prongs with an opening between to allow the lead 106 to pass through the opening while the lead anchor 108 is sitting on the retention hook.

In an example operation of the lead anchor, a lead 106 of a stimulation device 100 is threaded through a lead anchor 108 and the distal end of the lead incorporates, or is attached to, an array 104 of electrodes 148 located at the desired location within the patient being treated. FIG. 1 illustrates schematically an implantable stimulation device 100, such as a spinal cord stimulator. The other end of the lead 106 is coupled to a control module 102 (or to a lead extension which is in turn coupled to the control module.) The medical practitioner or technician locates the lead anchor 108 to the desired area of attachment to the tissue 134 and uses a surgical crimping tool 136 or another suitable instrument to crimp the ends of the one or more fasteners 126 and 128 towards each other, thereby attaching the lead anchor 108 to the patient's tissue 134. In at least some embodiments, this entire procedure can be completed in a fraction of the time needed to implant a stimulation device using conventional lead anchors. This procedure may also be less invasive than implantation procedures requiring the use of sutures and the like.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A lead anchor, comprising:
   a body having an outer surface and defining a lead lumen extending between a first opening in a first end and a second opening in a second end, wherein the body is formed from an elastomeric material; and
   one or more fasteners partially disposed through at least one hole in the body such that at least a portion of each of the one or more fasteners extends beneath the outer surface of the body, wherein at least one of the one or more fasteners comprises at least two fastener ends that are disposed external to the outer surface of the body and that extend outwardly from opposing sides of the outer surface of the body when a lead is disposed in the lead lumen of the body and anchored to patient tissue, wherein when the body and the portion of the lead disposed in the lead lumen are positioned adjacent to patient tissue the at least two external, outwardly-extending fastener ends disposed on opposing sides of the outer surface of the body are configured and arranged to be squeezed together against the outer surface of the body on opposing sides of the body such that at least one of the fastener ends pierces the patient tissue to anchor the lead to the adjacent tissue, and wherein squeezing the at least two external, outwardly-extending fastener ends together against the outer surface of the body on opposing sides of the body compresses the body against the portion of the lead disposed in the lead lumen of the body to prevent the portion of the lead disposed in the lead lumen from moving relative to the body.

2. The lead anchor of claim 1, wherein the elastomeric material is polyurethane, silicone, or a combination thereof.

3. The lead anchor of claim 1, wherein the one or more fasteners are molded into the body when the body is formed.

4. The lead anchor of claim 1, wherein the one or more fasteners have sharp fastener ends.

5. The lead anchor of claim 1, wherein the lead anchor comprises a plurality of the fasteners.

6. A method of implanting an implantable stimulation device, the method comprising:
   implanting a lead comprising an electrode array at the distal end of the lead extending from the electrode array; and
   anchoring the lead to the surrounding tissue using the lead anchor of claim 1 by squeezing together the fastener ends of at least one of the one or more fasteners against the outer surface of the body on opposing sides of the body.

7. The method of claim 6, further comprising implanting a control module.

8. The method of claim 6, further comprising coupling the electrode array to a control module using the lead.

9. The method of claim 6, wherein the one or more fasteners have sharp ends.

10. A system, comprising:
an implantable stimulation device comprising a control module, an electrode array, a lead for coupling the control module to the electrode array, and one or more lead anchors of claim 1.

11. The system according to claim 10, wherein the lead anchor is configured and arranged to anchor the lead to patient tissue such that the lead and the electrode array do not pierce the patient tissue.

12. A kit, comprising:
a lead and one or more lead anchors of claim 1.

13. The kit according to claim 12, further comprising a control module for coupling to the lead.

14. The kit according to claim 12, further comprising an electrode array for coupling to the lead.

15. The kit according to claim 12, wherein the body of at least one of the one or more lead anchors is made of silicone, polyurethane, or a combination thereof.

16. The kit according to claim 12, wherein the one or more fasteners are molded into the body when the body is formed.

17. The kit according to claim 12, wherein the one or more fasteners have sharp fastener ends.

18. The kit according to claim 12, further comprising a surgical crimping tool, the surgical tool comprising:
at least two gripping elements for squeezing together the outwardly-extending fastener ends of one or more fasteners of the one or more lead anchors; and
a retention hook coupled to the gripping elements, wherein the retention hook is configured and arranged to position the one or more lead anchors relative to the gripping elements to clear the lead disposed in the one or more lead anchors.

19. The kit according to claim 18, wherein the gripping elements comprise a pair of handles fastened at a hinge element to form squeeze grips.

20. The kit according to claim 18, further comprising a travel stop coupled to the gripping elements, wherein the travel stop is configured and arranged to stop the crimping action of the surgical tool when the protruding ends of the fasteners have been closed sufficiently to secure the one or more lead anchors to patient tissue.

* * * * *